US009937191B2

(12) United States Patent
Heneine et al.

(10) Patent No.: US 9,937,191 B2
(45) Date of Patent: *Apr. 10, 2018

(54) INHIBITION OF HIV INFECTION THROUGH CHEMOPROPHYLAXIS

(71) Applicant: THE UNITED STATES OF AMERICA, as represented by the Secretary, Department of Health and Human Services, Washington, DC (US)

(72) Inventors: Walid Heneine, Atlanta, GA (US);
Thomas M. Folks, Helotes, TX (US);
Robert Janssen, Atlanta, GA (US);
Ronald A. Otten, Villa Rica, GA (US);
Jose Gerardo Garcia Lerma, Decatur, GA (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/406,344

(22) Filed: Jan. 13, 2017

(65) Prior Publication Data

US 2017/0143745 A1      May 25, 2017

Related U.S. Application Data

(63) Continuation of application No. 14/679,887, filed on Apr. 6, 2015, now Pat. No. 9,579,333, which is a
(Continued)

(51) Int. Cl.
*A61K 31/675* (2006.01)
*A61K 31/505* (2006.01)
(Continued)

(52) U.S. Cl.
CPC .......... *A61K 31/675* (2013.01); *A61K 9/0053* (2013.01); *A61K 31/513* (2013.01)

(58) Field of Classification Search
CPC .......................... A61K 31/7072; A61K 31/676
(Continued)

(56) References Cited

U.S. PATENT DOCUMENTS

| 5,814,639 | A | 9/1998 | Liotta et al. |
| 5,914,331 | A | 6/1999 | Liotta et al. |

(Continued)

FOREIGN PATENT DOCUMENTS

| CA | 2512475 | 8/2004 |
| WO | WO 1996/01110 | 1/1996 |

(Continued)

OTHER PUBLICATIONS

Grant et al., "Promote HIV chemoprophylaxis research, don't prevent it," *Science* 309(5744): 2170-2171 (Sep. 29, 2005).
(Continued)

*Primary Examiner* — Shengjun Wang
(74) *Attorney, Agent, or Firm* — Klarquist Sparkman, LLP

(57) ABSTRACT

A process is provided for protecting a primate host from a self-replicating infection by an immunodeficiency retrovirus. Protection is achieved by administering to the primate host a combination of a pharmaceutically effective amount of a nucleoside reverse transcriptase inhibitor and a pharmaceutically effective amount of a nucleotide reverse transcriptase inhibitor prior to exposure to the immunodeficiency retrovirus. The administration is effective if provided in a single dose within 24 hours of the exposure. A regime of regular daily doses is also effective in providing protection against an immunodeficiency retrovirus becoming self-replicating after infecting a primate host. A process for
(Continued)

controlling retrovirus transmission within a population includes the administration to a subpopulation at high risk for contracting an immunodeficiency retroviral infection the detailed combination prior to sexual exposure to a source of immunodeficiency retrovirus so as to preclude the immunodeficiency retrovirus from becoming self-replicating in a member of the subpopulation.

19 Claims, 4 Drawing Sheets

Related U.S. Application Data continuation of application No. 11/669,547, filed on Jan. 31, 2007, now Pat. No. 9,044,509.

(60) Provisional application No. 60/764,811, filed on Feb. 3, 2006.

(51) Int. Cl.
   *A61K 31/513* (2006.01)
   *A61K 9/00* (2006.01)
(58) Field of Classification Search
   USPC .................................................. 514/81, 274
   See application file for complete search history.

(56) References Cited

U.S. PATENT DOCUMENTS

| | | | |
|---|---|---|---|
| 5,922,695 | A | 7/1999 | Arimilli et al. |
| 5,935,946 | A | 8/1999 | Munger, Jr. et al. |
| 5,977,089 | A | 11/1999 | Arimilli et al. |
| 6,043,230 | A | 3/2000 | Arimilli et al. |
| 6,642,245 | B1 | 11/2003 | Liotta et al. |
| 6,703,396 | B1 | 3/2004 | Liotta et al. |
| 9,044,509 | B2 | 6/2015 | Heneine et al. |
| 2004/0224917 | A1 | 11/2004 | Dahl et al. |

FOREIGN PATENT DOCUMENTS

| | | |
|---|---|---|
| WO | WO 2004/002498 | 1/2004 |
| WO | WO 2004/064845 | 8/2004 |
| WO | WO 2005/021001 | 3/2005 |

OTHER PUBLICATIONS

Youle et al., "Could chemoprophylaxis be used as an HIV prevention strategy while we wait for an effective vaccine?," *AIDS* 17(6): 937-938 (Apr. 11, 2003).
Youle et al., "Pre-exposure chemoprophylaxis (PREP) as an HIV prevention strategy," *JIAPAC* 2(3): 102-105 (Jul./Sep. 2003).
Collins "Tenofovir/FTC backbone outperforms AZT/3TC (Combivir) with efavirenz in treatment naive patients; reduced toxicity drives ITT viral efficacy," *HIV Treatment Bulletin* (2 pages printed from http://i-base.info/htb/7665)(Jan. 29, 2005).
Panlilio et al., "Updated U.S. public health guidelines for the management of occupational exposure to HIV and recommunication for post exposure prophylaxis," *MMWR* 54(RR09): (25 pages) (Sep. 30, 2005).
Smith et al., "Antiretroviral postexposure prophylaxis after sexual, injection-drug use, or other nonoccupational exposure to HIV in the United States," *MMRW* 54(RR-2) (28 pages)(Jan. 21, 2005).
Szekeres et al., "Anticipating the efficacy of HIV pre-exposure prophylaxis," (PrEP) and the needs of at-risk Californians, *PrEP and the Needs of At-risk Californians* (40 pages)(Nov. 2004).
Van Rompay et al., "Two low doses of tenofovir protect newborn macaques against oral simian immunodeficiency virus infection," *Journal of Infectious Diseases* 184: 429-438 (Aug. 15, 2001).

Kellerman et al., "Knowledge and use of HIV pre-exposure prophylaxis among attendees of minority gay pride events, 2004," *J. Acquir. Immune. Defic .Syndr.* 43(3): 376-377 (Nov. 1, 2006).
"Retrovirus-induced immunodeficiencies," Coffin et al., (eds) in *Retroviruses NCBI Bookshelf,* Cold Spring Harbor Laboratory Press, Cold Spring Harbor, NY, pp. 1-6, (1997).
Aids Patient Care and SIDs 16(8): 401 (2002).
Andrews et al., "Long-acting integrase inhibitor protects macaques from intrarectal simian/human immunodeficiency virus," *Science* 343(6175):1151-1154 (Mar. 7, 2014).
*Biomedical Primate Research Centre,* printout of website information, http://www.bprc.nl/en/aids-hiv/ (printed to PDF on Dec. 23, 2015).
Birnbaum et al., "Rectal absorption of lamotrigine compressed tablets," *Epilepsia* 41(7):850-853 (Jul. 2000).
Buster et al., "Doctor-to-Patient Transmission of Hepatitis B Virus: The Potential of Antiviral Therapy for Prevention," *Scandinavian Journal of Gastroenterology* 241:45-49 (2004).
Collier "Efficacy of Combination Antiviral Therapy," Advances in Experimental Medicine and Biology 394:355-372 (1996).
Communication of a Notice of Opposition and Opposition Brief from corresponding European Patent No. 2,015,753, 38 pp. (dated Feb. 6, 2014).
Connor et al., "Reduction of Maternal-Infant Transmission of Human Immunodeficiency Virus Type 1 with Zidovudine Treatment," *Wayne State University Libraries, The New England Journal of Medicine* 331(18):1173-80 (Nov. 3, 1994).
Domingo et al., "A 48-week study of fat molecular alterations in HIV naive patients starting tenofovir/emtricitabine with lopinavir/ritonavir or efavirenz," *J. Acquir. Immune. Defic. Syndr.* 66(5):457-65 (Aug. 15, 2014).
*European Medicines Agency,* Committee for Medicinal Products for Human Use (CHMP), Refection paper on the non-clinical and clinical development for oral and topical HIV pre-exposure prophylaxis (PrEP), pp. 1-8 (Mar. 15, 2012).
Fung et al, "Tenofovir disoproxil fumarate: A nucleotide reverse transcriptase inhibitor for the treatment of HIV infection," *Clinical Therapeutics* 24(10):1515-1548 (2002).
Garcia-Lerma and Heneine, "Animal models of antiretroviral prophylaxis for HIV prevention," *Current Opinion* 7(6):505-513 (2012).
Garcia-Lerma et al., "Intermittent Prophylaxis with Oral Truvada Protects Macques from Rectal SHIV Infection," *Sci. Transl. Med.* 2(14):1-8 (Jan. 13, 2010).
Garcia-Lerma et al., "Prevention of Rectal SHIV Transmission in Macaques by Daily or Intermittent Prophylaxis with Emtricitabine and Tenofovir" *PLoS* 5(2)(e28):1-9 (Feb. 2008).
Gianotti et al., "Impact of a treatment including tenofovir plus didanosine on the selection of the 65R mutation in highly drug-experienced HIV-infected patients," *AIDS* 18(16):2205-2208 (Nov. 5, 2004).
*Gilead,* Press Releases, printout of website information, "Gilead announces preclinical data for an investigational TLR7 agonist in SIV-infected virally suppressed monkeys," http://www.gilead.com/news/press-releases/2015/2/gilead-announces-preclinical-data-for-an-investigational-t1r7-agonist-in-sivinfected-virally-suppressed-monkeys (printed to PDF on Dec. 23, 2015).
Grant et al., "Preexposure Chemoprophylaxis for HIV Prevention in Men Who Have Sex with Men," *New England J. Med.* 363:2587-2599 (2010).
Grant et al., "Promote HIV Chemoprophylaxis Research, Don't Prevent It" *Science* 309(5744):2170-2171 (Sep. 30, 2005) (Abstract only).
Harouse et al., "Mucosal transmission and induction of simian AIDS by CCR5-specific simian/human immunodeficiency virus SHIV(SF162P3)," *J. Virol.* 275(4):1990-1995 (Feb. 2001).
Harouse, et al., "Distinct Pathogenic Sequela in Rhesus Macaques Infected with CCR5 or CXCR4 Utilizing SHIVs," *Science* 284:816-819 (1999).
Hoogewerf et al., "Change to abacavir-lamivudine-tenofovir combination treatment in patients with HIV-1 who had complete virological suppression," *The Lancet* 362:1979-1980 (Dec. 13, 2003).

(56) References Cited

OTHER PUBLICATIONS

Johnson et al., "A Rapid and Sensitive Real-time PCR Assay for the K65R Drug Resistance Mutation in SIV Reverse Transcriptase," *AIDS Research and Human Retroviruses* 22(9):912-916 (2006).
Keegan, "Existing HIV Drug Holds Promise for Prevention," Southern Voice (Apr. 7, 2006).
Levin, "Prevention of Rectal SHIV Transmission in Macaques by Tenofovir/FTC Combination," *Conference on Retroviruses and Opportunistic Infections* 13:1-4 (Feb. 5-8, 2006).
Luciw, et al., "Persistent Infection of Rhesus Macaques With T-Cell-Line-Tropic and Macrophage-tropic Clones of Simian/Human Immunodeficiency Viruses (SHIV)," *Proc. Natl. Acad. Sci. USA* 92:7490-7494 (Aug. 1995).
Martinez et al., "Pancreatic toxic effects associated with co-administration of didanosine and tenofovir in HIV-infecte3d adults," *The Lancet* 364:65-67 (Jul. 3, 2004).
Massud et al., "Lack of Prophylactic Efficacy of Oral Maraviroc in Macaques despite High Drug Concentrations in Rectal Tissues," *Journal of Virology* 87(16):8952-8961 (Aug. 2013).
Merchant, "Update on Emerging Infections: News from the Centers for Disease Control and Prevention," *Annals of Emergency Medicine* 46(1):82-86 (Jul. 2005).
Molina et al, "On-demand preexposure prophylaxis in men at high risk for HIV-1 infection," *N. Engl. J. Med.* 373(23):2237-2246 (Dec. 3, 2015).
Otten et al., "Efficacy of Postexposure Prophylaxis after Intravaginal Exposure of Pig-Tailed Macaques to a Human-Derived Retrovirus Human Immunodeficiency Virus Type 2," *Journal of Virology* 9771-9775 (Oct. 2000).
Otten et al., "Multiple Vaginal Exposures to Low Doses of R5 Simian-Human Immunodeficiency Virus: Strategy to Study HIV Preclinical Interventions in Nonhuman Primates," *JID* 191:164-173 (Jan. 15, 2005).
Perrino et al., "Pharmacokinetics, tolerability, and safety of intranasal administration of reformulated OXYCONTIN® tablets compared with original OXYCONTIN® tablets in healthy adults," *Clin. Drug Investig.* 33(6):441-449 (Jun. 2013).
Pilcher et al., "Brief by Efficient Acute HIV Infection and the Sexual Transmission of HIV," *JID* 189:1785-1792 (May 15, 2004).
Shaporio et al., "Highly Active Antiretroviral Therapy Started During Pregnancy or Postpartum Suppresses HIV-1 RNA, but not DNA, in Breast Milk," *Journal of Infectious Diseases* 192:713-719 (Sep. 1, 2005).
Simian immunodeficiency virus, *Wikipedia* (encyclopedia description) (obtained on Dec. 4, 2015).
Smith, "Pre-exposure Chemoprophylaxis for HIV: It is Time," *Retrovirology* 1(16):1-5 (Jul. 6, 2004).
Stephenson "New HIV Prevention Strategies Urged," JAMA 292(10):1163-1164 (2004).
Subbarao, et al., "Chemoprophylaxis with Tenofovir Disoproxil Fumarate Provided Partial Protection against Infection with Simian Human Immunodeficiency Virus in Macaques Given Multiple Virus Challenges," *JID* 194:904-911 (Oct. 1, 2006).
TRUVADA™ (Emtricitabine and Tenofovir Disoproxial Fumarate), Prescribing Information for *NDA* 21-752:6 (Jul. 2004).
Tsai et al., "Effect of Dosing Frequency on ZDV Prophylaxis in Macaques Infected with Simian Immunodeficiency Virus," *Journal of Acquired Immune Deficiency Syndromes* 6(10):1086-1092 (1993).
Tsai et al., "Effectiveness of Postinoculation (R)-9-(2-Phosphonylmethoxypropyl) Adenine Treatment for Prevention of Persistent Simian Immunodeficiency Virus SIV Infection Depends Critically on Timing of Initiation and Duration of Treatment," *Journal of Virology* 4265-4273 (May 1998).
Tsai, et al., "Prevention of SIV Infection in Macaques by (R)-9-(2-Phosphonylmethoxypropyf) adenine," *Science* 270:1197-1199 (Nov. 17, 1995).
Veazey et al., "Protection of macaques from vaginal SHIV challenge by vaginally delivered inhibitors of virus-cell fusion," *Nature* 438(7064):99-102 and 8 pages of supplemental information (Nov. 3, 2005).
Wang et al., "Pharmacokinetic and Pharmacodynamic Characteristics of Emtricitabine Support its Once Daily Dosing for the Treatment of HIV Infection," *AIDS Research and Human Retroviruses* 20(11):1173-1182 (Nov. 2014).
Wang et al., "Single-dose sertaconazole vaginal tablet treatment of vulvovaginal candidiasis," *J. Chin. Med. Assoc.* 69(6):259-63 (Jun. 2006).
Winston et al., "The Use of a Triple Nucleoside-nucleotide Regimen for Nonoccupational HIV Post-exposure Prophylaxis," *HIV Medicine* 6:191-97 (2005).

INHIBITION OF HIV INFECTION THROUGH CHEMOPROPHYLAXIS

CROSS-REFERENCE TO RELATED APPLICATIONS

This is a continuation U.S. patent application Ser. No. 14/679,887, filed on Apr. 6, 2015, which is a continuation of U.S. patent application Ser. No. 11/669,547, filed on Jan. 31, 2007, issued as U.S. Pat. No. 9,044,509, which in turn claims the benefit of U.S. provisional application 60/764,811, filed on Feb. 3, 2006. All of the prior applications are incorporated herein by reference in their entirety.

GOVERNMENT INTEREST

The invention described herein may be manufactured, used, and licensed by or for the United States Government.

FIELD OF THE INVENTION

The present invention in general relates to a process for inhibiting initial infection by a retrovirus such as human immunodeficiency virus (HIV) and in particular to a combination of a nucleoside reverse transcriptase inhibitor (NRTI) and a nucleotide reverse transcriptase inhibitor (NtRTI) capable of preventing self-replicating retroviral infection, even in response to multiple viral challenges.

BACKGROUND OF THE INVENTION

Despite the fact that significant progress has been made slowing the advancement of the symptoms of AIDS associated with HIV infection, in the absence of an effective vaccine, HIV continues to spread globally. The spread of HIV persists in part because an infected individual remains a potential source of injection. It is clear that current treatment of monitoring viral titer and in response to a titer exceeding a preselected threshold commencing treatment with highly active antiretroviral therapy (HAART) has not prevented new infections.

An attractive method of controlling the spread of HIV would be to provide an individual exposed to a potential source of HIV with a pre-exposure prophylactic treatment. As HIV and, in particular HIV-1, often begins with a comparatively small population of retroviral particles being transmitted to a new host and within a few days self-replicating into a retroviral titer detectable in host blood serum. If the establishment of a retroviral could be blocked before the HIV burden expands into a self-propagating infection, an individual could avoid contraction of HIV.

Previous attempts at pre-exposure prophylaxis have met with limited success. Prophylactic activity has been demonstrated with the NtRTI, tenofovir in monkey models challenged with simian immunodeficiency virus (SIV).[1-3] Unfortunately, oral daily dosing and pre-exposure prophylaxis with tenofovir at a dose equivalent to that used in humans proved to only be partially protective against rectal SHIV transmission.[4]

HAART therapy involves the administration of a combination including at least three active compounds classified by the mode of operation as an NRTI, an NtRTIs, a non-nucleoside reverse transcriptase inhibitors (NNRTIs), protease inhibitor, and an entry inhibitor. While HAART is effective in lowering retroviral titer in a host, concerns remain as to the long term toxicity and the retained potential to infect others. It is also unknown if initiating HAART therapy in a pre-exposure prophylactic regimen would be efficacious. As a result, society remains devoid of a pre-exposure prophylactic regimen to prevent an individual from developing self-propagating retrovirus infection subsequent to initial exposure.

Thus, there exists a need for a chemoprophylactic composition and dosing regimen effective in blocking early stage infection by retrovirus in a host founder cell population. There also exists a need for a chemoprophylactic composition formulated with a vehicle amenable to user compliance.

SUMMARY OF THE INVENTION

A process is provided for protecting a primate host from a self-replicating infection by an immunodeficiency retrovirus. Protection is achieved by administering to the primate host a combination of a pharmaceutically effective amount of a nucleoside reverse transcriptase inhibitor and a pharmaceutically effective amount of a nucleotide reverse transcriptase inhibitor prior to exposure to the immunodeficiency retrovirus. The administration is effective if provided in a single dose prior to the exposure. A regime of multiple temporally spaced doses prior to retroviral exposure is also effective in providing protection against an immunodeficiency retrovirus becoming self-replicating after infecting a primate host. A process for controlling retrovirus transmission within a population includes the administration to a subpopulation at high risk for contracting an immunodeficiency retroviral infection a combination of a pharmaceutically effective nucleoside reverse transcriptase inhibitor and a pharmaceutically effective amount of a nucleotide reverse transcriptase inhibitor prior to exposure to a source of immunodeficiency retrovirus so as to preclude the immunodeficiency retrovirus from becoming self-replicating in a member of the subpopulation.

A kit is also provided that includes at least one combination dose of a pharmaceutically effective amount of a nucleoside reverse transcriptase inhibitor and a pharmaceutically effective amount of a nucleotide reverse transcriptase inhibitor sufficient to protect a primate host from developing a self-replicating retroviral infection along with instructions for the administration of the at least one dose one prior to and optionally one additional dose subsequent to a potential exposure to an immunodeficiency retrovirus along with dosing modifications associated with subject characteristics and behaviors to further reduce the risk of contracting a self-replicating immunodeficiency retrovirus infection.

DETAILED DESCRIPTION OF THE PREFERRED EMBODIMENTS

Figure 1:
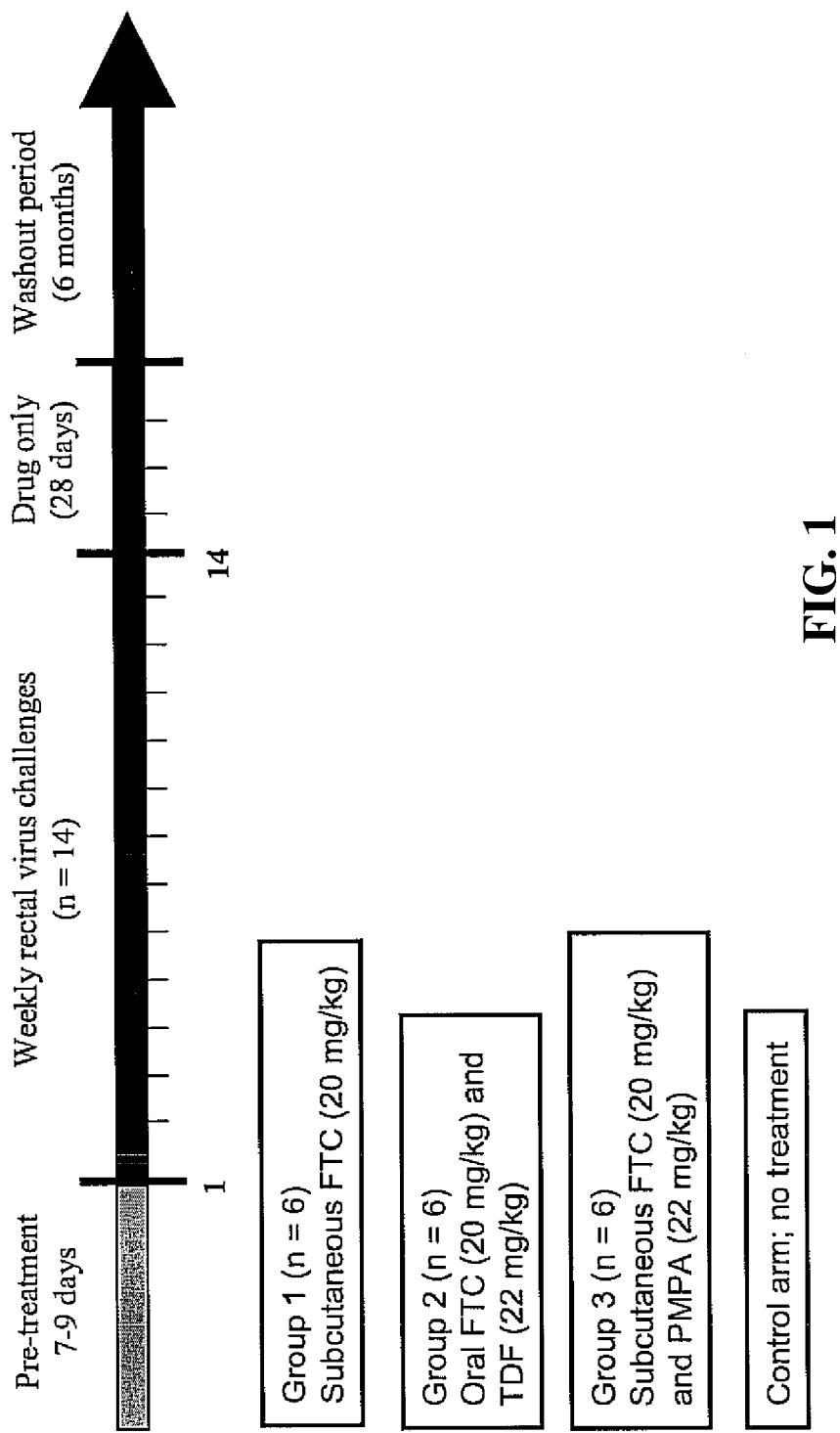
FIG. 1 is a schematic depicting one study of the present invention for 4 groups of macaques in which all treated macaques received known antiretroviral medications 7 to 9 days prior to the first virus inoculation and continuing throughout the study with treated animals that remained uninfected throughout the 14 viral challenges receiving 28 additional days of post-exposure prophylactics.

The present invention has utility in protecting a primate host from self-propagating immunodeficiency virus infection. The use of a combination of antiretroviral agents as a prophylactic dosing regime is also provided for the manufacture of a medicament is provided for protection against a human immunodeficiency virus infection developing to a level of self-replicating infection. Retroviral transmission through most routes entails a new primate host receiving a small number of viral particles. Common routes of retrovirus transmission illustratively include sexual intercourse, medical worker skin puncture inoculation, hypodermic needle sharing, blood transfusions, birth canal exposure, breastfeeding, and transplacental contact between individuals. Through the administration of at least one nucleoside reverse transcriptase inhibitor (NRTI) and at least one nucleotide reverse transcriptase inhibitor (NtRTI) prior to a retrovirus exposure protection is provided against development of a self-replicating retroviral infection. As the aforementioned exposure routes are characterized by a small number of retrovirus particles being transferred to the new primate host, this initial phase of infection represents a window of opportunity to protect a host from infection. The inventive chemoprophylactic treatment is provided through a dosing regimen. A dosing regimen according to the present invention that provides retroviral protection to a host primate includes at least one single dose administered prior to initial retroviral exposure. An inventive dosing regimen also includes a course of multiple doses administered in advance of exposure to maintain a therapeutic level of NRTI and NtRTI agents in the primate host. The timing of the at least one does prior to retroviral exposure is dictated by the pharmacokinetics of the NRTI and NtRTI components to assure the presence of a therapeutically effective amount of inventive composition for at least 20 hours subsequent to the exposure to the communicated small retroviral particle population. Multiple doses are administered according to the present invention at regular time intervals and amounts such as for example like formulated daily doses for a period of several days, weeks, or months; or are administered in advance of a likely exposure as a cluster of doses, with the amount of NRTI and NtRTI components in each dose being independent of the of amount of NRTI and NtRTI in other doses within the cluster. While most oral, topical, and parenteral existing versions of NRTIs and NtRTIs are fully absorbed and therapeutically active within 1 to 8 hours, it is appreciated that subcutaneous implants and long acting timed release formulations allow for a single dose to sustain therapeutically effective amounts of an inventive prophylactic composition for several days, weeks, or even months. Representative of sustained release compositions and implants are provided in the U.S. Pat. Nos. 4,122,129; 4,927,687; 4,996,047; 5,169,642; and 5,656,296.

The combination of NRTI and NtRTI compounds administered prophylactically according to the present invention are shown to provide a dose-dependent inhibition of HIV self-replicating infection and a therapeutically effective dosing primate host protection against self-replicating HIV infection is provided, even in response to multiple viral challenges. While the present invention is largely detailed with respect to HIV-1 as a prototypical infectious and pathogenic retrovirus, it is appreciated that other retroviruses owing to reliance on reverse transcription for replication are also protected against in a primate host according to the present invention.

As used herein, "protection" as used in the context of a host primate response to an immunodeficiency virus challenge is defined by the host primate being serologically negative and negative in response to a polymerase chain reaction (PCR) testing for viral genome.

As used herein, the term "retrovirus" is inclusive of any virus that utilizes reverse transcriptase in the viral replication cycle and therefore is susceptible to the antiviral activity of nucleoside or nucleotide analogs specifically inclusive of HIV (HIV-1 and HIV-2), HTLV-1, HTLV-2, HTLV-3, HTLV-4, and SIV. Also encompassed are viruses such as HBV that although not technically classified as retroviruses nonetheless utilize a reverse transcriptase and are therefore susceptible to the antiviral activity of nucleoside and/or nucleotide analogs.

As used herein a "primate host" is defined to include a monkey, baboon, chimpanzee, gorilla, and a human. Non-human primates are appreciated to themselves be susceptible to infection by retroviruses and in particular immunodeficiency viruses and represent well-established animal models as to human response with an appreciation that physiological differences often require different doses in milligrams per kilogram for a nonhuman primate animal model relative to a human.

The compositions of the present invention include administration in combination of an NRTI and NtRTI and are readily compounded by pharmaceutical composition with conventional pharmaceutically acceptable carriers or diluents. Additionally, pharmaceutically acceptable derivatives and prodrugs of active NRTIs and NtRTIs operative in the present invention include salts such as alkali metal salts; esters such as acetate, butyrate, octinoate, palmitate, chlorobenzoates, benzoates, $C_1$-$C_6$ benzoates, succinates, and mesylate; salts of such esters; and nitrile oxides. It is appreciated that other analogs of pharmaceutically active NRTIs or NtRTIs that provide within a primate host an active antiviral metabolite residue are also suitable as part of an inventive composition. A pharmaceutically acceptable carrier or diluent includes agents that are compatible with other ingredients of a dosage and not injurious to a primate host. The identity and process for compounding a combination of at least one NRTI and at least one NtRTI into a dosage form suitable for delivery by a route with administration by oral, rectal, topical, vaginal or parenteral routes of administration are provided in Remington's Science and Practice of Pharmacology, $20^{th}$ Edition, Chapters 37-47, pages 681-929, where parenteral injection includes subcutaneous, intramuscular, intravenous, and intradermal injection.

As used herein the term "prodrug" is defined to include a compound that when administered to a primate host generates an active NRTI or NtRTI as a result of spontaneous reaction under physiological conditions, enzymatic catalysis, metabolic clearance, or combinations thereof. An exemplary NtRTI prodrug currently FDA approved for HAART use is tenofovir disoproxil fumarate (TDF) and is detailed in U.S. Pat. No. 5,935,946.

The present invention provides an alternative to conventional retroviral therapy using HAART, in response to self-propagating HIV infection by protecting a primate host against the establishment of self-replicating retroviral infection that provides an indication for such therapy. Through prophylactic prior dosing with an inventive combination including at least one NRTI and one NtRTI, replication of the comparatively low number of viral particles received by a host primate is prevented.

To achieve protection against a primate host developing a retroviral self-replicating infection, at least one dosage of an NRTI and NtRTI is administered to the primate host prior to exposure to the retrovirus. Preferably, the at least one NRTI and at least one NtRTI are administered concurrently. More preferably, the combination of reverse transcriptase inhibitors is compounded into a single formulation.

The process of the present invention demonstrates protection against retroviral self-replicating infection through administration of even a single dosage administered prior to the retroviral exposure. Owing to the known pK rates of specific NRTIs and NtRTIs, a single dosage is administered to assure a therapeutically effective amount of NRTI and NtRTI persist in the primate host for a time of more than 12 hours after viral challenge. With conventional NRTI and NtRTI formulations, currently approved for HAART, preferably an inventive dose is administered within 12 hours prior to retroviral exposure and still more preferably often within 2 hours prior to retroviral exposure. The practice of the inventive process involving the administration of a single dosage in the hours proceeding a likely retroviral exposure is particularly advantageous in assuring compliant dosing in a human and also avoids side effects associated with a regular dosing regime and is particularly well suited for a human engaging in a sporadic behavior likely to bring the person into retroviral exposure. Preferably, an additional dose or doses of a combination of at least one NRTI and at least one NtRTIs is provided subsequent to the retroviral exposure event to assure adequate antiviral reverse transcriptase inhibitor concentration during and immediately subsequent to retroviral infection of the host founder cell population so as to preclude retroviral self-replication to assure NRTI and NtRTI incorporation into a replicating virus genome. Preferably, a dose of an inventive composition taken after retroviral exposure is administered within 24 hours subsequent to the exposure, and more preferably within 12 hours subsequent to the exposure.

Alternatively, an individual routinely subjected to retroviral exposure can be protected against the development of a self-replicating retroviral infection through administration of regular prophylactic doses of an inventive combination. As a result, an epidemiological advantage exists in controlling the outbreak and spread of a retrovirus within a population is provided through offering routine doses of an inventive composition prophylactically to high-risk persons such as sex workers and a short course prophylactic inventive composition to uninfected sex trade clientele.

It is appreciated that hybrid dosing regimes of an inventive composition are also operative herein and include multiple doses prior to retroviral exposure with multiple doses not being administered for a duration or with sufficient periodicity to arise to the level of a routine prophylactic regime.

The at least one nucleoside reverse transcriptase inhibitor has the attribute of interfering with in vivo viral replication. An NRTI operative in an inventive prophylactic process includes emtricitabine, lamivudine, zalcitabine, zidovudine, azidothymidine, didanosine, stavudine, abacavir; with the aforementioned specific NRTIs intended to include pharmaceutically acceptable salts, esters, ester salts, nitrile oxides, and prodrugs of any of the active agents.

An at least one nucleotide reverse transcriptase inhibitor (NRTI) present in an inventive composition to protect a primate from developing a self-replicating retroviral infection illustratively includes tenofovir, adefovir; 2',3'-dideoxy-3'-fluoroadenisine; 2',3'-dideoxy-3'-fluoroguanasine; 3'deoxy-3'-fluoro-5-O-[2-(L-valyloxy)-propionyl]guanosine with the aforementioned specific NtRTIs intended to include pharmaceutically acceptable salts, esters, ester salts, nitrile oxides, and prodrugs of any of the active agents.

Optionally, an inventive composition also includes within an inventive combination other antiretrovirals such as non-nucleoside reverse transcriptase inhibitors, protease inhibitors, fusion inhibitors, and combinations thereof. Representative non-nucleoside reverse transcriptase inhibitors operative herein illustratively include delavirdine, efavirenz, nevirapine, and other diarylpyrimidine (DAPY) derivatives. Representative protease inhibitors operative herein illustratively include amprenavir, tipranavir, indinavir, saquinavir, lopinavir, ritonavir, fosamprenavir calcium, ritonavir, atazanavir sulfate nelfinavir mesylate, and combinations thereof. An entry inhibitor operative herein as an optional active ingredient in an inventive composition illustratively includes enfuvirtide, Schering C (Schering Plough), S-1360 (Shionogi), and BMS806 (Bristol Myers Squibb).

The dose of individual active components of an inventive prophylactic composition is administered to create a therapeutic concentration of the active composition at the situs of retrovirus initial founder cell population infection prior to viral exposure. It is appreciated that establishing a therapeutic concentration at the time of viral replication for a given NRTI, NtRTI or optional additional active agent in the target cells, includes factors for the therapeutic agent such as the route of administration, pharmacokinetics, absorption rate based on administration route, effects of food on oral absorption, in vivo distribution, metabolic pathways, elimination route, race, gender, and age of the subject, single dose incident side effects, long term administration side effects, and synergistic effects with co-administered active agents. Information related to these factors considered in dosing are available from the United States Food and Drug Administration (http://www.fda.gov/oashi/aids/virals.html) Preferably, NRTI and NtRTI prophylactic dosing according to the present invention uses as a starting point the maximal recommended tolerated dosing levels for the given active agent combination associated with HAART treatment protocols.

An inventive kit is provided that includes a 2-dose package of oral doses, such as tablets. In an exemplary embodiment of FDA approved NRTI and NtRTIs, each dose contains between 100 and 2500 milligrams (mg) of emtricitabine and between 100 and 2500 mg of TDF along with instructions to ingest the first dose approximately 1 to 8 hours prior to potential retroviral exposure and preferably about 2 hours there before, and a second dosage to be ingested 20 to 48 hours after potential retroviral exposure, preferably at about 22 hours thereafter. For an adult human, preferably each of the doses includes 200 mg of emtricitabine and 300 mg TDF. A non-human primate dose according to the present invention is typically higher on a mg per kg animal body weight basis by a factor typically ranging from 2 to 10. Additional NRTIs, NtRTIs, NNRTIs, protease inhibitors or entry inhibitors are optionally provided in concert with either or both of these doses. The kit also includes instructions as to the timing of doses, contraindications, modifications associated with food ingestion, and additional behaviors that the recipient (synonymously described herein as a human primate host) can undertake to reduce the risk of retrovirus exposure and initial infection. It is also appreciated that a carrier illustratively including a gel, jelly, cream, ointment, film, sponge, foam, suppository, vaginal ring or other delivery device is provided containing an NRTI such as emtricitabine, alone or in combination with an NtRTI such as tenofovir or TDF. The carrier is readily applied to mucosal tissue likely to be exposed to viral transmission as an added level of protection in concert with the oral doses.

An inventive kit is also provided that includes at least one NRTI and at least one NtRTI compounded as a gel, jelly, cream, ointment, film, sponge, foam, suppository, or applied to a vaginal ring or other like antiviral barrier. To prepare such a pharmaceutical compounded form, an effective amount of each of the active agents inclusive of at least one NRTI and NtRTI is combined in admixture with the pharmaceutically acceptable carrier or applied to a surface of the barrier. It is appreciated that the residence time of such a pharmaceutical composition is maintained at the site of administration through the inclusion of an optional bioadhesive that provides adhesion to mucosal tissue or the dermis. An inventive composition compounded for application to the dermis or mucosal tissue is provided along with instructions as to the timing of doses, contraindications, modifications associated with food ingestion, and additional behaviors that the person (synonymously described herein as a human primate host) can undertake to reduce the risk of retrovirus exposure and initial infection. Optionally, a kit containing an oral dosage is combined with a composition compounded for application to the dermis, rectal mucosa or vaginal mucosa so as to assure a therapeutically effective combination of NRTI and NtRTI at the mucosal point of retroviral entry associated with sexual exposure, as well as a therapeutically effective serum circulating quantity of prophylactic antiretrovirals.

The present invention is further detailed with respect to the following non-limiting examples. These examples are intended to provide exemplary specific embodiments of the present invention and are not intended to limit the scope of the appended claims.

EXAMPLES

Example 1—Antiretroviral Drugs and Doses

A dose of 22 mg/kg of tenofovir disoproxil fumarate (TDF) is given orally and 20 mg/kg of emtricitabine (FTC) given orally or subcutaneously to one group of adult male rhesus macaques. The 22 mg/kg TDF dose resulted in an area-under the plasma concentration-time curve over a 24 h interval (AUC) of 4.49 µg×hr/ml which was similar to the value of 5.02 µg×hr/ml observed in human receiving 300 mg of TDF. The dose of 20 mg/kg of FTC resulted in an AUC value (11 µg×hr/ml), also similar to that observed in humans receiving 200 mg of FTC orally (10.0±3.12 µg×hr/ml)[6]. Subcutaneous administration of FTC results in plasma FTC levels comparable to those achieved during oral administration, indicating a high FTC absorption in rhesus macaques.

Oral administration of FTC and TDF to macaques is by mixing the drug powders with peanut butter or fruit. Macaques are observed to ensure ingestion.

Example 2—Virus Inoculations

A chimeric envelope $SHIV_{SF162P3}$ isolate is used to inoculate the macaques. $SHIV_{SF162P3}$ is a construct that contains the tat, rev, and env coding regions of $HIV-1_{sF162}$ in a background of SIVmac239. This isolate was obtained from the National Institutes of Health (NIH) AIDS Research and Reference Reagent Program.[7,8] Virus exposures are performed 2 hours after drug treatment, and involved non-traumatic inoculation of 1 mL of $SHIV_{SF162P3}$ (10 TCID50 or $7.5\times10^6$ viral RNA copies) into the rectal vault via a sterile gastric feeding tube.[9] Anesthetized macaques remained recumbent for at least 15 min after each intra-rectal inoculation.

Example 3—SHIV Viral Load Assay

Plasma RNA is quantified using a real-time PCR assay as previously described.[5] This assay has a sensitivity of detection of 50 RNA copies/ml or 10 copies of a pVp1 plasmid carrying the SIVmac239 RT gene. HIV-1 RNA is extracted from 1 mL of plasma using the NucliSens extraction method (bioMérieux). A known amount of virus particles ($3\times10^5$) from an HIV-1 CM240 virus stock is added to each sample prior to extraction to control for the efficiency of extraction. Reverse transcription is performed using 10 microliters (µl) of extracted RNA and the 2-step TaqMan Gold reverse-transcriptase (RT)-PCR kit (Applied Biosystems) according to the manufacturer's instructions. PCR reactions are performed as described using an ABI 7000 Gene Detection System (Applied Biosystems). Virus loads are calculated from a standard curve generated with known amount of virus particles. All primers and probes used for SIVmac239 and HIV-1 CM240 have been reported elsewhere.[5] HIV-1 CM240 is obtained from the National Institutes of Health (NIH) AIDS Research and Reference Reagent Program.

Example 4—Detection of Genotypic Resistance to FTC and Tenofovir

Emergence of FTC and tenofovir resistance is monitored by sequence analysis of SIV RT (551 bp; amino acids 52 to 234) and by a more sensitive allele-specific real-time PCR method for the K65R and M184V mutations. Sequence analysis was done from plasma viruses using an RT-PCR procedure as previously described.[5] The Vector NTI program (Version 7, 2001) is used to analyze the data and to determine deduced amino-acid sequences. Detection of low frequency of K65R and M184V mutants in plasma by real-time PCR is performed as previously described.[10] These assays have a detection limit of 0.4% of K65R and 0.6% of M184V cloned sequences in a background of wild type plasmid.

Example 5—Virus-Specific Antibody Responses

Virus-specific serologic responses (IgG and IgM) are measured using a synthetic-peptide EIA (Genetic Systems HIV-1/HIV-2) assay.

Example 6—Statistical Methods

The exact log-rank test is used for a discrete-time survival analysis of the treatment and control groups, with use of the number of inoculations as the time variable. The Cox proportional hazards model is used to estimate the relative hazard ratio (HR). Percent protection is calculated from the HR value using the formula: $(1-1/HR)\times100$. All statistical analyses for calculation of the efficacy of the different interventions are performed using SAS software (version 9.1; SAS Institute) and StatXact software (version 6.3; Cytel).

Example 7—Routine Dosing Experimental Design

Macaques are exposed rectally once weekly for up to 14 weeks to SHIV162p3 which contains an R5 tropic HIV-1 envelope that resembles naturally transmitted viruses. The SHIV162p3 challenge dose is 10 TCID50 or $7.6 \times 10^5$ RNA copies which is similar to HIV-1 RNA levels in semen during acute infection in humans.[11] Virus exposures are terminated when a macaque became infected. FIG. 1 shows the study design and the interventions evaluated in each group of macaques. Three prophylactic drug treatments of increasing drug potency are each given once daily to a group of six macaques. Animals in Group 1 were treated subcutaneously with 20 mg/kg of FTC alone. Animals in Group 2 received orally a combination of FTC (20 mg/kg) and TDF (22 mg/kg). Animals in Group 3 had the most protective treatment with subcutaneous 20 mg/kg of FTC and a 22 mg/kg of tenofovir (PMPA). The rate of infection in each group is compared with that seen in 18 untreated control macaques (9 real time and 9 historical controls).

All treated macaques received the corresponding drugs 7 to 9 days prior to the first virus inoculation to achieve steady-state plasma levels. Treated animals that remained uninfected during the 14 challenges received 28 days of post-exposure prophylaxis after the last challenge. Protection was defined as absence of persistent viremia and seroconversion. Treated animals that became infected continued treatment for an average of 21 weeks (range=13 to 29) to monitor for plasma viremia and drug resistance development.

Example 8—Survival Curves

Figure 2:
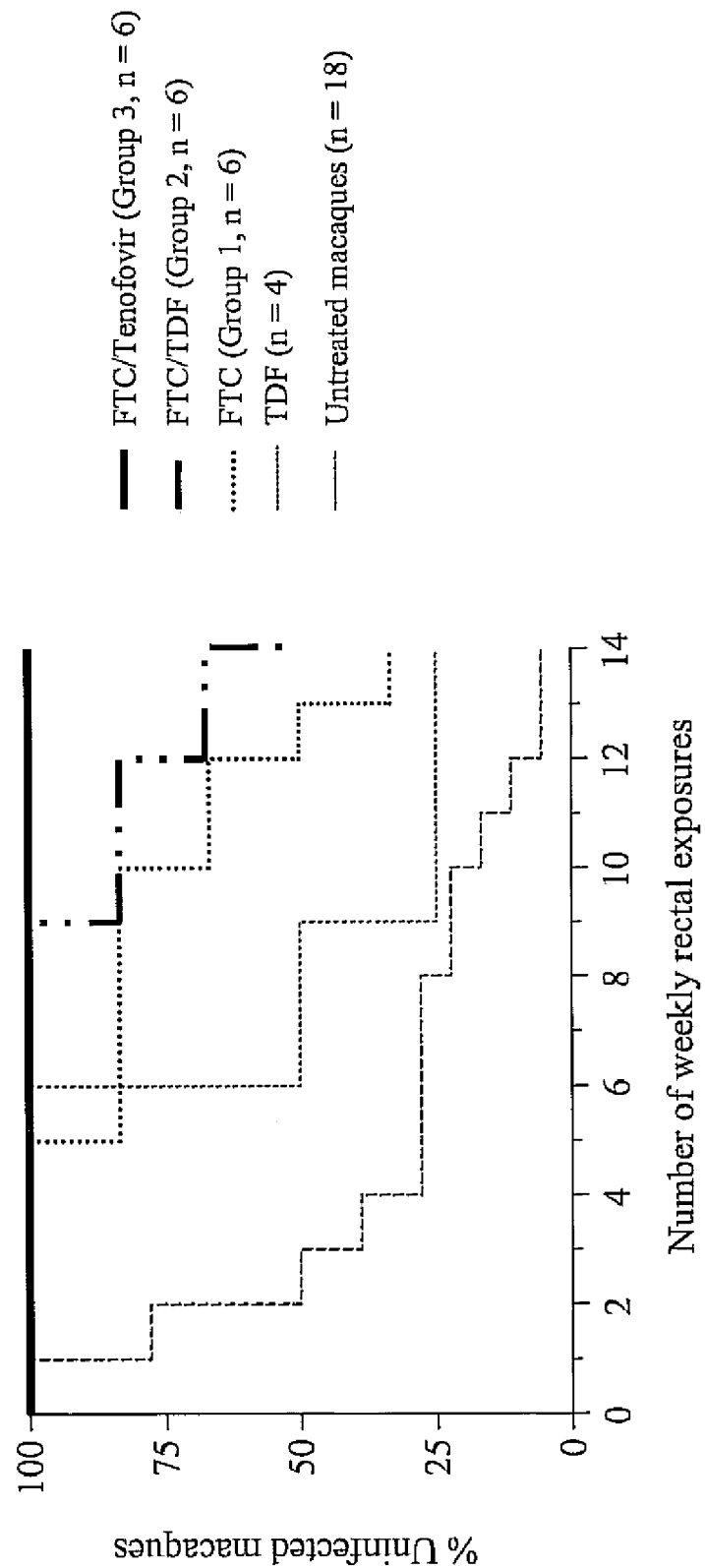
FIG. 2 is a survival curve graph for macaque Groups 1-4 per FIG. 1, as well as for animals receiving only tenofovir disoproxil fumarate (TDF).

FIG. 2 shows the survival curves observed for each group of animals per Example 7. Data with TDF (20 mg/kg) is also provided for comparison. Untreated macaques are infected after a median of 2 rectal exposures (mean=4). The majority of the animals (13/18 or 72%) are infected during the first 4 challenges (median=2); 4 (22%) are infected between exposures 8 and 14 (mean=10), and only 1 (6%) remained uninfected after 14 exposures. The median 2 exposures for infection in controls suggests that an animal receiving prophylactic treatment and remaining uninfected after 14 virus challenges would have been protected against a median of 7 rounds of transmissions. Treatments of Groups 1-3 are all protective to a degree with a clear dose-response relationship being observed. All 6 macaques in Group 3 that received the most potent inventive composition remained uninfected demonstrating that full protection against repeated challenges is possible. Of the 6 macaques in Group 2, 4 were protected and only 2 (animal reference numbers AI-54 and AG-81) became infected at exposures 9 and 12. Compared to controls, infection in this group is reduced by 7.8-fold (Cox proportional hazard ratio [HR]=7.8, p=0.0075). Infection in both animals is significantly delayed compared to the untreated controls (p=0.0004). These 2 macaques became seropositive 2 weeks after the first detectable viral RNA in plasma and both were proviral DNA positive at weeks 10 and 12, respectively. Of the 6 macaques in Group 1 receiving FTC only, 2 remained protected after 14 exposures and 4 had the first detectable viral RNA at exposures 5 (AG-80), 10 (AG-46), 12 (AH-04), and 13 (AG-07), respectively. Survival analysis showed a statistically significant difference from untreated controls (p=0.004). Compared to controls, infection is reduced 3.8-fold macaques (Cox proportional hazard ratio [HR]=3.8, p=0.021). Infection in these 4 animals is also confirmed by PCR amplification of proviral DNA from PBMCs and by serology; antibody responses are detectable 3, 1, 2, and 6 weeks after the first detectable RNA, respectively. FIG. 2 also shows that the protection achieved with FTC alone was higher than that previously seen in 4 animals receiving TDF,[5] consistent with the slightly higher potency of FTC, although the difference was not statistically significant (p=0.5).

Example 9—Prophylactic Breakthrough Infections and Drug Resistance Emergence

Figure 3:
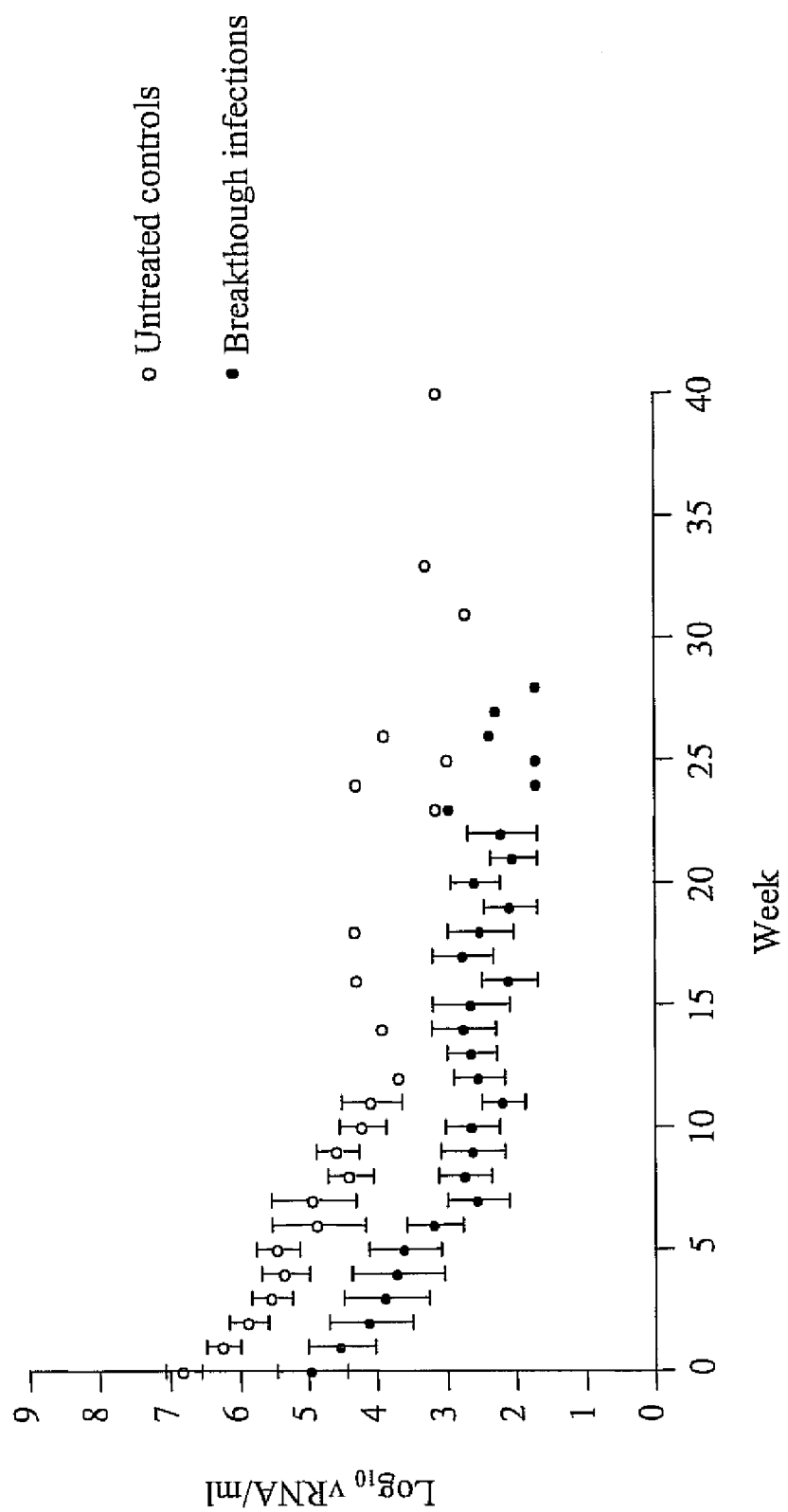
FIG. 3 is a graph depicting a plot of viremia as a function of time for untreated controls (○) and breakthrough infections (●) where each point represents a mean viremia observed, 0 time indicates peak plasma virus load observed in a given animal where the arrow bars denote standard error of the mean (SEM).
Figure 4:
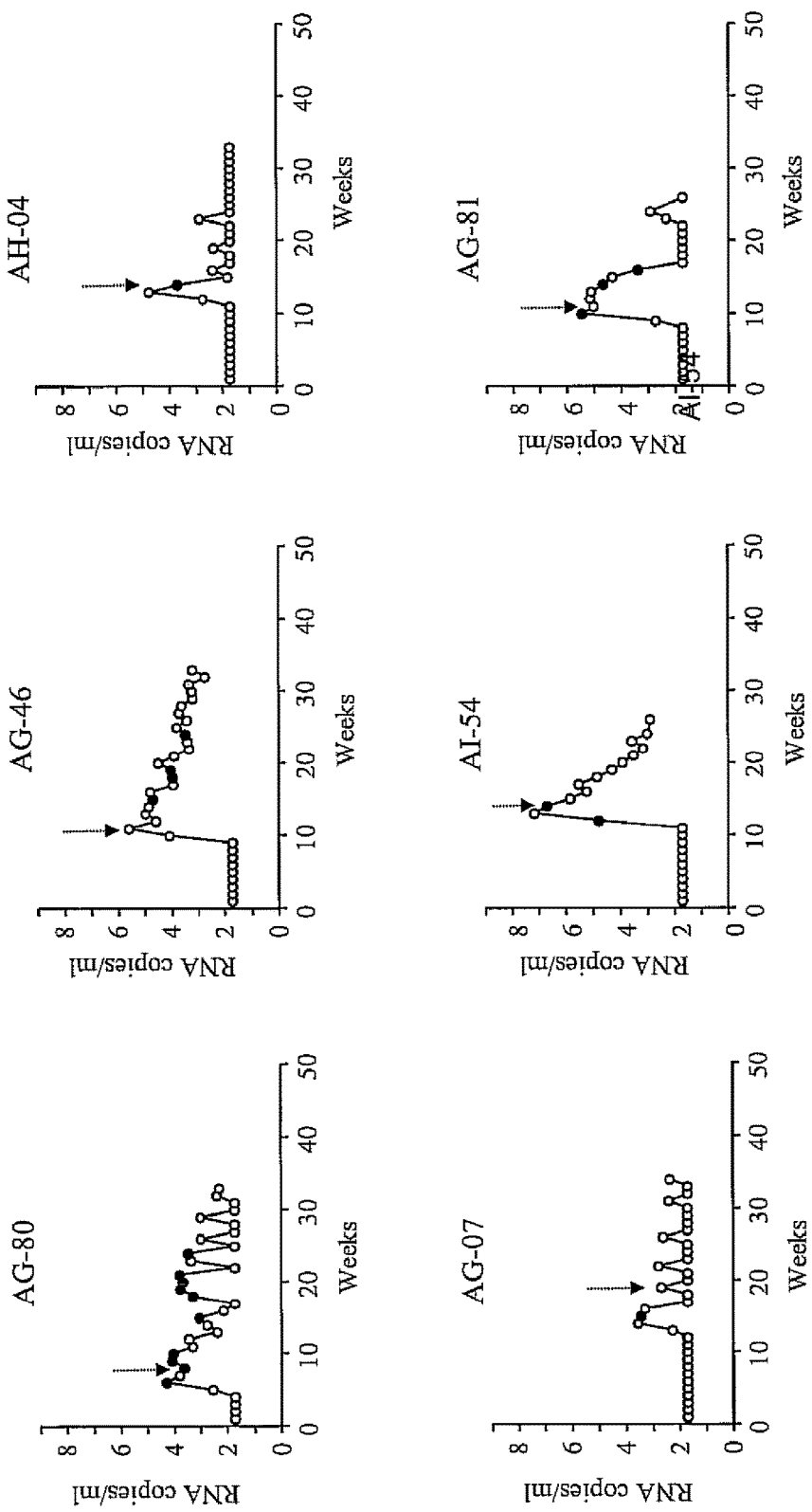
FIG. 4 depicts plots of infection dynamics as a function of time during the study per FIG. 1 with plots for animals coded as AG-80, AG-46, AH-04 and AG-07 corresponding to emtricitabine (FTC) treatment alone, or FTC plus TDF treatment (AI-54 and AG-81). The arrow indicates the first detectable antibody response. Grey circles indicate detectable M184V/I mutation; wild type sequences are shown in as black full circles. Open circles indicate the time points where no genotype was undertaken

Since the dynamics of breakthrough infections that occur during inventive prophylaxis and drug resistance emergence are unknown, the 6 infected animals from Groups 1 and 2 are followed under continued drug treatment. FIG. 3 compares the virus load kinetics in the 6 breakthrough infections with those in 12 untreated macaques that had sufficient follow-up samples. The mean peak viremia in the 6 treated macaques was $4.9 \pm 0.5$ $\log_{10}$ RNA copies/ml, $2.0$ $\log_{10}$ lower than in untreated controls ($6.9 \pm 0.3$ $\log_{10}$ RNA). FIG. 3 also shows that such differences in viremia were maintained up to week 11 as indicated by similar rate of virus load decline seen in the two groups of animals ($-0.23 \pm 0.02$ $\log_{10}$/week in treated vs. $-0.29 \pm 0.02$ $\log_{10}$/week in untreated controls). The individual virus load kinetics in the 6 breakthrough infections are shown in FIG. 4. Three FTC (AG-80, AH-04, and AG-07) and one of the FTC/TDF (AG-81) failures had undetectable virus loads 3, 4, 7, and 11 weeks after the peak in viremia, respectively; viremia in these animals remained consistently low or undetectable for up to 20 weeks. In contrast, all 12 untreated macaques had detectable virus loads during a median follow-up period of 7 weeks (range=5-36 weeks). The arrow in FIG. 4 denotes the first detectable antibody response. Grey circles indicate detectable M184V/I mutation; wild type sequences are shown in black full circles. Open circles are provided for data points not genotyped.

Drug resistance testing showed that wild type virus initiated all 6 breakthrough infections in Groups 1 and 2 reflecting residual virus replication in target cells not protected by drugs (FIG. 4). Four animals had no evidence of drug resistance despite extended treatment (median=23 weeks). Only 2 animals had detectable M184V (AG-46, FTC-treated) or M184I (AI-54 FTC/TDF-treated) mutations associated with FTC resistance at week 4 and 10, respectively. The tenofovir-associated K65R mutation is not detected in the 2 Group 2 animals receiving FTC/TDF. FIG. 4 also shows that the 2 macaques that selected M184V/I had the highest peak viremias. Without intending to be bound to a particular theory, it is hypothesized that more virus replication in these animals may have facilitated drug resistance selection. Reductions in acute viremia are proposed to contribute at a population level to a decrease in virus transmissibility.

Example 10—Single Dosing

The process of Example 7 is repeated in Group 3 with drugs only being administered 2 hours prior to and 22 hours subsequent to each inoculation. The resultant survival curves are comparable to those detailed in Example 8.

Example 11—Single Dosing with Suppository

A group of 6 macaques received the drug treatment of Group 3 per Example 7 in the form of a gel inserted rectally containing 300 mg of tenofovir and 300 mg lamuvidine (3-TC) 1 hour before viral inoculation with observation to assure that the suppository is not voided. The gel is formed by compounding tenofovir and 3-TC in 2% by weight hydroxyethyl cellulose (HEC)-based gel in both a vaginal formulation (pH 4.5) and rectal formulation (pH 6.5) containing (w/v) 3% tenofovir, and 3% 3-TC. The gels are stable at room temperature for at least five months with no loss in activity; and gels retained full activity at both pH 4.5 and pH 6.5 at levels equivalent to those observed for tenofovir and 3-TC preparations in water. Using an MT4/MTT phenotypic assay, all gels were tested for activity against wild-type HIV-1$_{HXB2}$, and resistant HIV-1 viruses containing the K65R or M184V mutations. No significant cytotoxicity is seen in the cervical explant model.

Viral protection of the macaques is maintained throughout the study.

REFERENCES CITED

1. Connor E M, S. R., Gelber R, Kiselev P, Scott G, O'Sullivan M J, VanDyke R, Bey M, Shearer W, Jacobson R L, Jimenez E, O'Neill E, Bazin B, Delfraissy J-F, Culnane M, Coombs R, Elkins M, Moye J, Stratton P, Balsley J, for The Pediatric AIDS Clinical Trials Group Protocol 076 Study Group Reduction of Maternal-Infant Transmission of Human Immunodeficiency Virus Type 1 with Zidovudine Treatment. N Engl J Med 331, 1173-1180 (1994).
2. Otten R A, Smith D K, Adams D R, Pullium J K, Jackson E, Kim C N, Jaffe H, Janssen R, Butera S, Folks T M. Efficacy of postexposure prophylaxis after intravaginal exposure of pig-tailed macaques to a human-derived retrovirus (human immunodeficiency virus type 2). J Virol. 74, 9771-5 (2000).
3. Tsai C C, Follis K E, Sabo A, Beck T W, Grant R F, Bischofberger N, Benveniste R E, Black R. Prevention of SIV infection in macaques by (R)-9-(2-phosphonyl-methoxypropyl)adenine. Science. 270, 1197-9 (1995).
4. Tsai C C, Emau P, Follis K E, Beck T W, Benveniste R E, Bischofberger N, Lifson J D, Morton W R. Effectiveness of postinoculation (R)-9-(2-phosphonylmethoxypropyl) adenine treatment for prevention of persistent simian immunodeficiency virus SIVmne infection depends critically on timing of initiation and duration of treatment. J Virol. 72, 4265-73 (1998).
5. Subbarao S, Otten R A, Ramos A, Kim C, Jackson E, Monsour M, Adams D R, Bashirian S, Johnson J, Soriano V, Rendon A, Hudgens M G, Butera S, Janssen R, Paxton L, Greenberg A E, Folks T M. Chemoprophylaxis with tenofovir disoproxil fumarate provided partial protection against Infection with simian human immunodeficiency virus in macaques given multiple virus challenges. J Infect Dis 194, 904-11 (2006).
6. Wang L H, Begley J, St Claire R L 3rd, Harris J, Wakeford C, Rousseau F S. Pharmacokinetic and pharmacodynamic characteristics of emtricitabine support its once daily dosing for the treatment of HIV infection. AIDS Res Hum Retroviruses 20, 1173-82 (2004).
7. Harouse J M, Gettie A, Tan R C, Blanchard J, Cheng-Mayer C. Distinct pathogenic sequela in rhesus macaques infected with CCR5 or CXCR4 utilizing SHIVs. Science 284, 816-9 (1999).
8. Luciw P A, Pratt-Lowe E, Shaw K E, Levy J A, Cheng-Mayer C. Persistent infection of rhesus macaques with T-cell-line-tropic and macrophage-tropic clones of simian/human immunodeficiency viruses (SHIV). Proc Natl Acad Sci USA. 92, 7490-4 (1995).
9. Otten R A, Adams D R, Kim C N, et al. Multiple vaginal exposures to low doses of R5 simian-human immunodeficiency virus: strategy to study HIV preclinical interventions in nonhuman primates. J Infect Dis. 19, 164-73 (2005).
10. Johnson J A, Rompay K K, Delwart E, Heneine W. A Rapid and Sensitive Real-Time PCR Assay for the K65R Drug Resistance Mutation in SIV Reverse Transcriptase. AIDS Res Hum Retroviruses 22, 912-6 (2006).
11. Pilcher C D, Tien H C, Eron J J Jr, Vernazza P L, Leu S Y, Stewart P W, Goh L E, Cohen M S. Brief but efficient: acute HIV infection and the sexual transmission of HIV. J Infect Dis. 189, 1785-92 (2004).

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of protecting a primate host from a self-replicating infection by an immunodeficiency retrovirus comprising:
    (a) selecting a primate host not infected with the immunodeficiency retrovirus, and
    (b) administering directly to an uninfected primate host a combination comprising:
        i. a pharmaceutically effective amount of emtricitabine; and
        ii. a pharmaceutically effective amount of tenofovir or tenofovir disoproxil fumarate,
    wherein the combination is administered orally in tablet form prior to the exposure of the primate host to the immunodeficiency retrovirus,
    thereby protecting the primate host from infection with the immunodeficiency retrovirus.
2. The process of claim 1, wherein selecting a primate host comprises selecting an adult human not infected with the immunodeficiency retrovirus.
3. The process of claim 2, wherein the adult human is a male.
4. The process of claim 2, wherein the pharmaceutically effective amount of emtricitabine and the pharmaceutically effective amount of tenofovir or the tenofovir disoproxil fumarate, are administered directly to the human in a combined single tablet.
5. The process of claim 2, wherein the immunodeficiency retrovirus is a human immunodeficiency virus.
6. The process of claim 5, wherein a humans immunodeficiency virus (HIV) is HIV-1.
7. The process of claim 1, wherein the combination is administered as preexposure prophylactic treatment prior to rectal and/or vaginal exposure of the primate host to the immunodeficiency retrovirus.
8. The process of claim 1, comprising administering 200 milligrams (mg) of emtricitabine to the primate host.

9. The process of claim 1, wherein the combination is administered daily for several days, weeks or months.

10. The process of claim 9, wherein the combination is administered daily for several days, weeks or months both before and after an exposure of the primate host to the immunodeficiency retrovirus.

11. The process of claim 1, wherein administration of the combination results in an absence of persistent viremia and seroconversion of the primate host.

12. The process of claim 4, wherein the tablet comprises 200 milligrams of emtricitabine and 300 mg of tenofovir disproxil fumarate.

13. A process for inhibiting establishment of a human immunodeficiency virus self-replicating infection of human immunodeficiency virus infection in a human, comprising:
  (a) selecting an uninfected human that does not have the self-replicating infection; and
  (b) administering to the uninfected human a combination comprising:
    i. a pharmaceutically effective amount of emtricitabine in a tablet; and
    ii. a pharmaceutically effective amount of tenofovir or a tenofovir disoproxil fumarate in a tablet;
  thereby inhibiting the establishment of the self-replicating infection with the immunodeficiency virus in the human, wherein the combination is administered prior to a potential exposure of the human to the human immunodeficiency retrovirus.

14. The process of claim 13, wherein the combination is compounded into a single tablet.

15. The process of claim 13, wherein an inhibition of infection in the host is determined by an absence of persistent viremia and seroconversion in the human following the exposure to the immunodeficiency retrovirus.

16. The process of claim 13, wherein the potential exposure to the human immunodeficiency retrovirus comprises sexual intercourse, medical worker skin puncture inoculation, hypodermic needle sharing, or blood transfusion.

17. The process of claim 13, wherein:
  (i) the pharmaceutically effective amount of emtricitabine; and
  (ii) the pharmaceutically effective amount of tenofovir or tenofovir disoproxil fumarate; are formulated in a single tablet.

18. The process of claim 17, wherein the tablet comprises 200 milligrams of emtricitabine and 300 mg of tenofovir disproxil fumarate.

19. The process of claim 17, wherein the tablet is administered daily for several days, weeks or months both before and after an exposure of the primate host to the immunodeficiency retrovirus.

* * * * *

UNITED STATES PATENT AND TRADEMARK OFFICE
CERTIFICATE OF CORRECTION

PATENT NO. : 9,937,191 B2
APPLICATION NO. : 15/406344
DATED : April 10, 2018
INVENTOR(S) : Walid M. Heneine et al.

It is certified that error appears in the above-identified patent and that said Letters Patent is hereby corrected as shown below:

In the Specification

Column 1, Line 37, "potential source of injection" should read --potential source of infection--.

Column 3, Line 44, "one does prior" should read --one dose prior--.

In the Claims

Column 12, Line 60, Claim 6, "wherein a humans" should read --wherein the human--.

Signed and Sealed this
Eighteenth Day of September, 2018

Andrei Iancu
*Director of the United States Patent and Trademark Office*

UNITED STATES PATENT AND TRADEMARK OFFICE
CERTIFICATE OF CORRECTION

PATENT NO. : 9,937,191 B2  
APPLICATION NO. : 15/406344  
DATED : April 10, 2018  
INVENTOR(S) : Heneine et al.

It is certified that error appears in the above-identified patent and that said Letters Patent is hereby corrected as shown below:

In the Claims

Claim 13, Column 13, beginning at Line 13: "A process for inhibiting establishment of a human immunodeficiency virus self-replicating infection of human immunodeficiency virus infection in a human, comprising:" should read --A process for inhibiting establishment of a human immunodeficiency virus self-replicating infection in a human, comprising:--.

Signed and Sealed this  
Nineteenth Day of April, 2022

Katherine Kelly Vidal  
*Director of the United States Patent and Trademark Office*